United States Patent
Ewing et al.

(10) Patent No.: US 10,119,937 B2
(45) Date of Patent: Nov. 6, 2018

(54) METHOD FOR DETECTING ORGANOPHOSPHORUS COMPOUNDS AND ILLICIT DRUGS

(71) Applicant: BATTELLE MEMORIAL INSTITUTE, Richland, WA (US)

(72) Inventors: Robert G. Ewing, Kennewick, WA (US); Blandina R. Valenzuela, Richland, WA (US); David A. Atkinson, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 133 days.

(21) Appl. No.: 15/211,752

(22) Filed: Jul. 15, 2016

(65) Prior Publication Data
US 2018/0017529 A1    Jan. 18, 2018

(51) Int. Cl.
*G01N 27/62* (2006.01)
*G01N 33/00* (2006.01)

(52) U.S. Cl.
CPC ....... *G01N 27/622* (2013.01); *G01N 33/0047* (2013.01)

(58) Field of Classification Search
CPC ....... G01N 27/622; G01N 27/62; G01N 27/00
USPC ........................................................ 436/173
See application file for complete search history.

(56) References Cited

U.S. PATENT DOCUMENTS

| 5,234,838 A | 8/1993 | Bacon, Jr. |
| 9,123,520 B2 | 9/2015 | Ewing et al. |
| 2008/0149824 A1* | 6/2008 | Miller .................. G01N 27/624 250/287 |
| 2013/0260478 A1 | 10/2013 | Ewing et al. |

FOREIGN PATENT DOCUMENTS

WO    WO00/52432    9/2000

OTHER PUBLICATIONS

Ewing, R. G., et al., Proton-bound cluster ions in ion mobility spectrometry, International Journal of Mass Spectrometry, 193, 1999, 57-68.
Puton, J., et al., Ion mobility spectrometers with doped gases, Talanta, 76, 2008, 978-987.
International Search Report and Written Opinion for PCT/US2017/028758, dated Aug. 1, 2017.
Keller et al., "Detection of designer drugs in human hair by ion mobility spectrometry (IMS)," Forensic Science international, 94(1-2):55-63 (Jun. 1998).
Satoh et al., "Ion mobility spectrometric analysis of vaporous chemical warfare agents by the instrument with corona discharge ionization ammonia dopant ambient temperature operation," *Analytica Chimica Acta*, 865:39-52 (Mar. 2015).
(Continued)

*Primary Examiner* — Christine T Mui
(74) *Attorney, Agent, or Firm* — Klarquist Sparkman, LLP (57) ABSTRACT

A method is disclosed for detecting organophosphorus compounds and illicit drugs using an ion detector. A vapor sample containing at least one analyte and at least one dopant is ionized. A proton-bound adduct ion is formed between the analyte and the dopant in a reaction region defined between the ionization source and the ion detector.

26 Claims, 10 Drawing Sheets

(56) References Cited

OTHER PUBLICATIONS

Verkouteren et al., "Reliability of ion mobility spectrometry for qualitative analysis of complex, multicomponent illicit drug samples," *Forensic Science International*, 206(1):190-196 (Aug. 2010).
Waraksa et al., "Dopants and gas modifiers in ion mobility spectrometry," *TrAC Trends in Analytical Chemistry*, 82:237-249 (Jun. 2016).

* cited by examiner

FIG. 2A — ROOM AIR
FIG. 2B — DMMP (NO RESPONSE)
FIG. 2C — TEA, TEA·H+ m/z 102
FIG. 2D — DMMP & TEA, TEA·H+ m/z 102, TEA·H+·DMMP m/z 226

METHOD FOR DETECTING ORGANOPHOSPHORUS COMPOUNDS AND ILLICIT DRUGS

STATEMENT REGARDING FEDERALLY SPONSORED RESEARCH OR DEVELOPMENT

This invention was made with Government support under Contract DE-AC0576RL01830 awarded by the U.S. Department of Energy. The Government has certain rights in the invention.

TECHNICAL FIELD

This invention relates to detection of organophosphorus compounds (OPCs) and illicit drugs. More specifically, this invention relates to detection of OPCs and illicit drugs using an ion detector and unique chemistry including proton affinity, chemical functionality, and chemical structure of the reaction dopant to improve selectivity and detection limits.

BACKGROUND

Low-level detection of illicit substances including narcotics and organophosphorus compounds (OPCs) remains a long-standing goal of modern instrument platforms. For example, detection of drugs at ultra-low levels significantly below those currently detected by state-of-the-art instrument systems analyzing swipe samples could enable vapor detection that would compete with a detection acuity on the order of sniffing dogs. Such systems would enable detection of vapors to identify illicit drugs in cargo containers and other concealed conveyances. And, ultra-low level detection of OPCs could also allow identification of hazardous compounds at levels well below those considered safe for the general population. However, positive detection of OPCs, for example, at these ultra-low concentrations can be masked by presence of other trace-level analytes in samples being tested. Accordingly, new methods are needed that provide accurate detection of OPCs and other important analytes at these ultra-low levels. The present invention addresses this need.

SUMMARY

The present invention is directed to methods for detecting organophosphorus compounds (OPCs) and illicit drugs.

In one embodiment, a method is disclosed for detecting organophosphorus compounds (OPCs) and illicit drugs with an ion detector. The ion detector may be, but is not limited to, for example, a mass spectrometer (MS) or an ion mobility spectrometer (IMS). The ion detector can be coupled to other instrument systems to increase selectivity. A preferred mass spectrometer for performing the method is an atmospheric flow tube (AFT) mass spectrometer (AFT-MS). The flow tube of the mass spectrometer includes a reaction region defined between an ionization source and the ion detector. The method includes introducing a vapor sample containing at least one analyte and at least one dopant into the flow tube, ionizing the vapor sample in the flow tube with an ionization source, and introducing the ionized vapor sample into the reaction region of the flow tube. The method also includes forming a proton-bound adduct ion that stems from the reaction between the at least one analyte and the at least one dopant in the reaction region. The method includes detecting the proton-bound adduct ion with the ion detector to confirm presence of the OPC and/or the illicit drug.

In some embodiments, the analyte is an organophosphorus compound (OPC) and the dopant includes a secondary or tertiary amine.

In some embodiments, the OPC is an organophosphate with various R-groups. In some embodiments, the organophosphorus compound is a phosphonate or an organophosphate with R groups typically containing between one and six carbons including, for example: dimethyl methyl phosphonate (DMMP), diisopropyl methyl phosphonate (DIMP), tributyl phosphate (TBP), triethyl phosphate (TEP), triphenylphosphate (TPhP), or combinations thereof. However, the invention is not intended to be limited thereto.

In some embodiments, the dopant is a dialkylamine, an alkyl-substituted derivative of pyridine, or a trialkylamine. In some embodiments, the dialkylamine or trialkylamine have R-groups typically between one and twelve carbons including, for example, diethylamine, diisopropyl amine, diethylmethyl amine, trimethylamine (TEA), tripropylamine, tributylamine (TBA), trioctylamine, tridecylamine, tridodecylamine, or combinations thereof. However, the invention is not intended to be limited thereto.

In some embodiments, amine dopants have a proton affinity greater than the OPC analytes. In some embodiments, amine dopants have a proton affinity greater than or equal to about 220 kcal/mol (920 kJ/mol). In some embodiments, amine dopants have a proton affinity in the range between about 220 kcal/mol (920 kJ/mol) to about 250 kcal/mol (1048 kJ/mol).

In some embodiments, the analyte is an illicit drug and the dopant is an OPC. In some embodiments, the illicit drug may contain at least one functional group that is an amine. In some embodiments, the illicit drug is a secondary or tertiary amine. In various embodiments, the illicit drug includes at least one of the following: heroin, cocaine, and methamphetamine. In some embodiments, the OPC dopant may be an organophosphate with R-groups typically containing between one to six carbons, including, for example: dimethyl methyl phosphate (DMMP), diisopropyl methyl phosphonate (DIMP), tributyl phosphate (TBP), triethyl phosphate (TEP), triphenylphosphate (TPhP), or combinations thereof. However, the invention is not intended to be limited thereto.

In some embodiments, OPCs are detectable in the AFT-MS at concentrations at 100 parts-per-quadrillion (ppq) or better.

In some embodiments, illicit drugs are detectable in the AFT-MS at concentrations at 160 parts-per-quadrillion (ppq) or better.

In some embodiments, OPCs are detectable in the IMS at concentrations at 50 parts-per-billion (ppb) or better.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

DETAILED DESCRIPTION OF THE PREFERRED EMBODIMENTS

The following description includes the preferred best mode of embodiments of the present invention. It will be clear from this description of the invention that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims. Disclosed are methods, systems, and apparatuses for detection of organophosphorus compounds and illicit drugs using a reaction tube that prolongs reaction times. In some embodiments, specific chemical dopants are used to form adducts that provide accessible detection limits while other compounds are detected directly without the use of dopants.

Figure 1A:
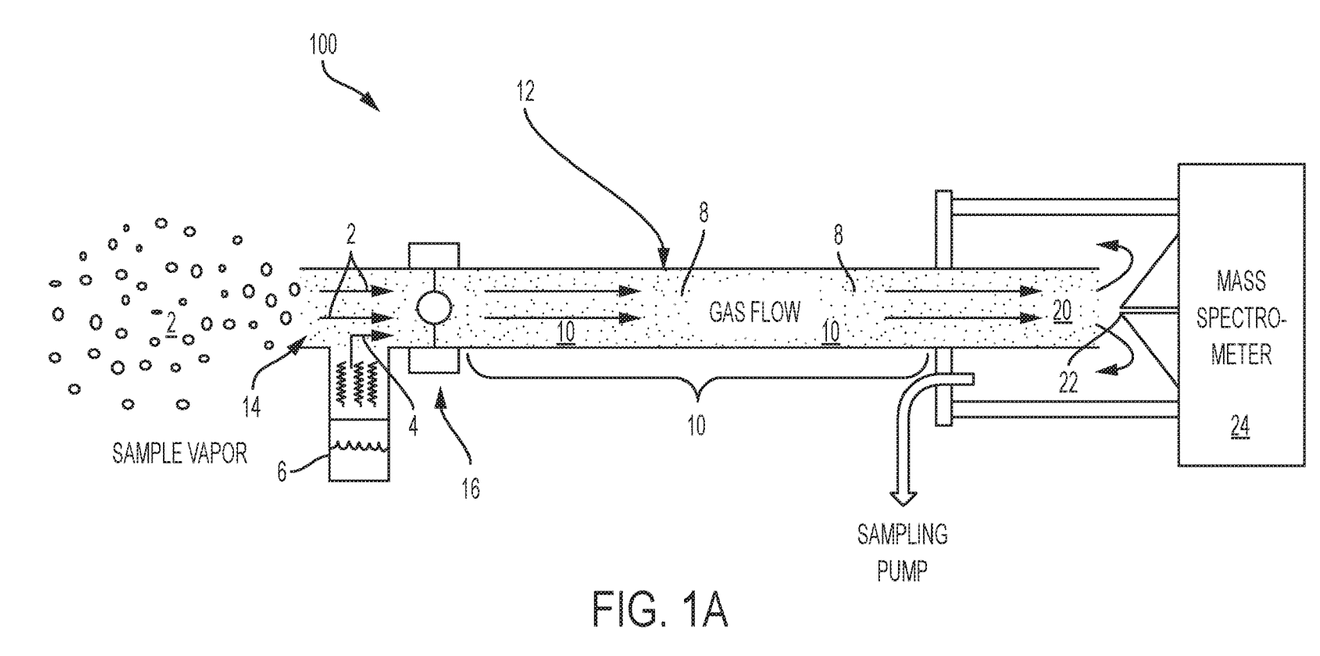
FIG. 1A is a schematic diagram of an Atmospheric Flow Tube Mass-spectrometry (AFT-MS) system for detecting vapors of OPCs and/or illicit drugs, in accordance with one embodiment of the present invention.

FIG. 1A is a schematic diagram of an exemplary AFT-MS system 100 for detecting OPCs and/or illicit drugs in concert with the present invention detailed in U.S. Pat. No. 9,123,520, which is incorporated in its entirety herein. The AFT-MS system delivers peak intensities corresponding to vapor data from detected threats. In the figure, sample vapors 2 containing analytes of interest may be introduced to a reaction region 10 of an atmospheric flow tube (AFT) 12 in various ways. In some embodiments, one or more analyte vapors of interest may be introduced to the reaction region, for example, through a sample gas inlet 14. In some embodiments, a sample gas including one or more analyte (sample) vapors 2 of interest and a selected dopant 4 (described further herein) from a dopant vapor source 6 all in the gas phase may be introduced to the reaction region 10, for example, through the sample gas inlet 14. Samples introduced for analysis may be pushed or pulled by suction (as shown). In the present invention, reactant ions generated by ionization of a carrier gas 8 with an ionization source 16 interact with (i.e., react) vapors of both the analyte 2 and dopant 4 when introduced into the reaction region 10. Positive ions are generated, for example, when a high energy electron emitted from the ionization source collides with the carrier gas and removes an electron from the carrier gas producing a positive ion, for example $N_2^+$. In the exemplary process, multiple collisions occur within the reaction region at or near atmospheric pressure resulting in a series of reactions that ultimately yield protonated species. However, pressures are not limited. Dopants, analytes, or other molecular species (e.g., contaminants) introduced in the reaction region may then be ionized by transfer of protons, which transfer is governed by relative proton affinities. Typically, molecular species with the highest proton affinity are observed. Along with proton transfer, ionization can occur via adduct formation between a protonated species and another compound. For example, adduct ions described herein are formed by reactions between analytes of interest (OPCs and/or illicit drugs) and added dopants (amines or OPCs). Detection of adduct ions confirms the presence of the analytes of interest.

In some embodiments, an analyte contained within a vial or other container and capable of emitting a vapor is placed in front of the sample gas inlet to the reaction region to introduce the analyte of interest thereto.

In some embodiments, an analyte vapor is present in an environment and is drawn directly into the sample gas inlet by suction.

In some embodiments, an analyte vapor is drawn directly into the inlet of the reaction region from the ambient environment by suction.

In some embodiments, a solid surface containing a surface residue(s) may be placed in front of the sample gas inlet to the reaction region. In some embodiments, a solid surface containing a solid sample may be placed in front of the sample gas inlet into the reaction region. Samples containing, e.g., OPCS and illicit drugs, can also be introduced into the reaction region in front of the ionization source, e.g., on various surfaces including, but not limited to, e.g., sample slides, sample swipes, and/or other solid surfaces. In some embodiments, samples in the form of surface residues and/or surface solids on a solid surface can be desorbed from the solid surface to transfer the residues and/or surface solids into the gas phase, for example, by application of heat.

A gas-phase sample may be introduced into the reaction region in a carrier gas that distributes within the reaction region. Carrier gases include, but are not limited to, e.g., air, nitrogen ($N_2$), argon (Ar), helium (He), oxygen ($O_2$), carbon dioxide ($CO_2$), other inert gases, and combinations of these various gases. In a preferred embodiment, the carrier gas includes ambient air. In some embodiments, a carrier gas may be used to introduce analyte vapors into the reaction region. Samples introduced as vapors can be carried by way of the carrier gas, e.g., from a carrier gas source, into the reaction region. In some embodiments, the reaction region may be defined between the ionization source and the detector. In some embodiments, the ionization source may be located in the reaction region downstream from where samples are introduced, but position is not intended to be limited. The ionization source ionizes the carrier gas in the reaction region, which produces reactant ions. These reactant ions further react with an added dopant to produce dopant ions that are selective (i.e., preferentially or selectively bind to) for target analytes of interest when present in the gas-phase sample introduced to the reaction region. In some embodiments, the ionization source also ionizes some fraction of the carrier gas, ambient gas, or dopants in the reaction region producing reactant ions. In some embodiments, the ionization source may be located adjacent to, and in front of, the reaction region, but position is not intended to be limited. Reactant ions (formed by ionization of clean air or carrier gas), analytes, and dopants when introduced into reaction region 10 react forming chemical adduct ions described herein that are subsequently detected in the mass spectrometer 24. Excess carrier gas exits the reaction region immediately prior to the inlet 22 of the mass spectrometer 24, but exit location is not limited thereto, as will be understood by those of ordinary skill in the mass-spectrometry arts. The reaction region may be of selected lengths that provide dopant ions a residence time sufficient to form chemical adduct ions with analyte molecules introduced in the carrier gas. Adduct ions are subsequently delivered to, and detected in, an ion detector, where the detection signal for chemical adduct ions of interest may be monitored and determined. The detector determines the presence or absence of the chemical adduct ion. Sensitivity or an increase in response could be improved by providing additional collisions between the reactant ions and analyte molecules. Number of collisions between the reactant ions is defined by the amount of time reactant ions and analyte molecules are present in the reaction region. Optimizing the detection signal for the chemical adduct ions when present includes adjusting the number of collisions between the reactant ions with the carrier gas containing the target analytes until the detection signal for the chemical adduct ions is above the signal background. In some embodiments, reactant ions move from the inlet to the detector by air flow, by an electric field, or by a combination of these approaches.

The AFT-MS detection system 100 of the present invention enhances sensitivity and selectivity at low parts-per-trillion (ppt) and parts-per-quadrillion (ppq) levels. For example, determination of the chemical adduct ions identifies the presence of the target analyte (e.g., OPCs and illicit drugs) in the vapor sample. In some embodiments, for example, analytes and/or dopants in a vapor sample can be detected at a concentration better than 100 parts-per-quadrillion (i.e., 100 parts in $10^{15}$ parts or 1 ppt) in less than 10 seconds.

Figure 1B:
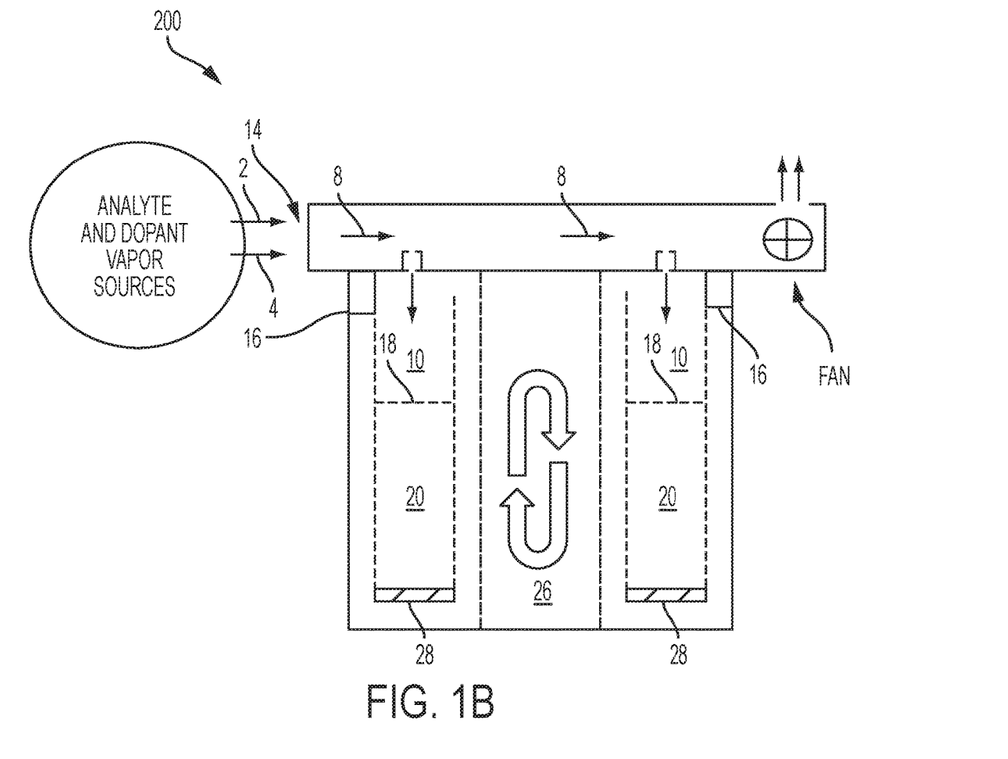
FIG. 1B is a schematic diagram of an ion-mobility system for detecting vapors of OPCs and/or illicit drugs, in accordance with another embodiment of the present invention.

FIG. 1B shows an exemplary IMS system 200 for detecting OPCs in concert with the present invention. The system includes a sample gas inlet 14, an ionization source 16, an ion gate 18, a reaction region 10, a drift region 20, and a Faraday detector 28. The system produces mobility spectra with peaks corresponding to vapors from the detected OPC threats. In the exemplary embodiment, ammonia-doped molecular sieves internal to the IMS instrument were replaced with non-doped molecular sieves 26 to generate unmodified reactant ions via ionization of clean air or carrier gas thus permitting selected dopants described herein to be introduced into the reaction region of the instrument.

In the present invention, reactant ions generated by ionization of the carrier gas 8 with ionization source 16 from interact with vapors of both the analyte 2 and dopant 4 when introduced into reaction region 10 positioned between ionization source 16 and ion gate 18. Positive ions are generated, for example, when a high energy electron emitted from the ionization source collides with the carrier gas and removes an electron from the carrier gas producing a positive ion, for example $N_2^+$. Dopants, analytes, or other molecular species (e.g., contaminants) introduced in the reaction region may then be ionized by proton transfer, which transfer is governed by relative proton affinities. In the exemplary process, multiple collisions occur within the reaction region at or near atmospheric pressure resulting in series of reactions that ultimately yield protonated species. However, pressures are not limited. In the exemplary embodiment, with the removal of the ammonia-doped molecular sieves, generated reactant ions typically form protonated water molecules. These reactant ions further react with added dopants which yield protonated dopant ions that are selective (i.e., preferentially or selectively bind to) for target analytes of interest when present in the gas-phase sample introduced to the reaction region. Added dopants then selectively bind to analytes of interest forming proton-bound adducts by reaction between the dopant and the analyte.

Figure 9:
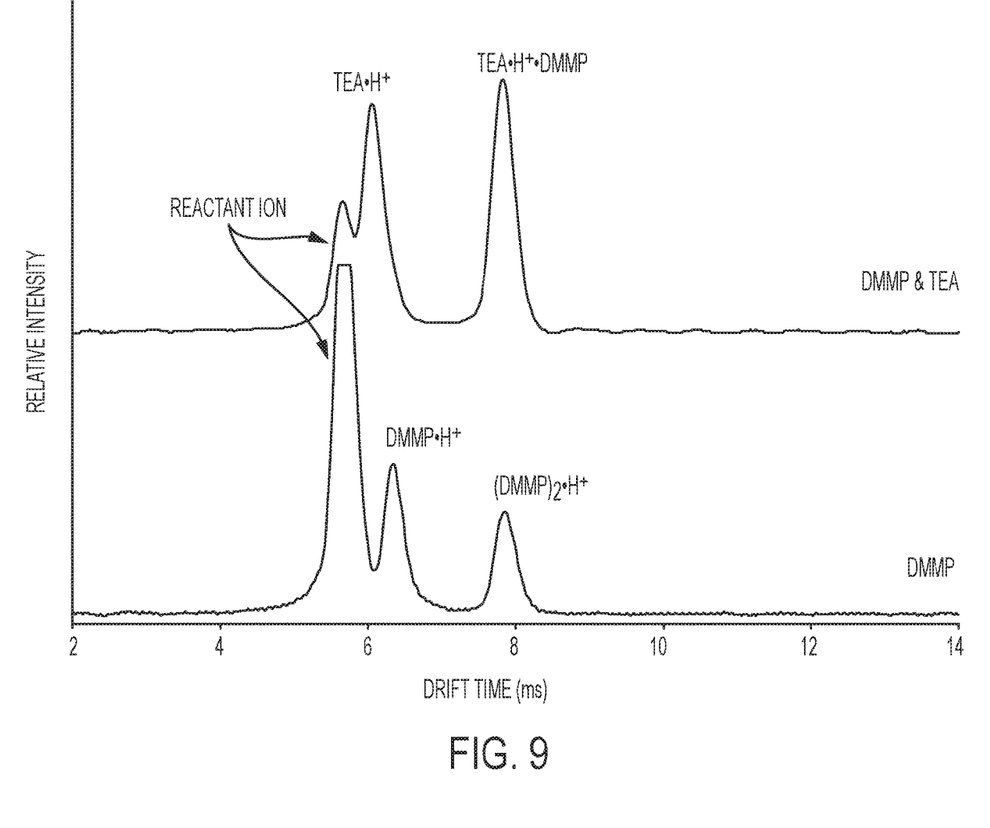
FIG. 9 compares IMS spectra for an exemplary OPC and the OPC in combination with an exemplary dopant used for detection of the OPC in concert with the present invention.

Resulting ions are introduced into the drift region 20 by pulsing ion gate 18. Introduced ions are then separated in the drift region based upon mobility in the gas phase. Ions are subsequently detected at the Faraday plate (detector) 28. Spectra generated subsequently include peaks in which mobility (observed as a function of drift time) can be linked to specific molecular species of interest. Intensity of the resulting peaks are related to concentration of the adduct ions of interest. Exemplary ion mobility spectra are shown in FIG. 9 described further herein.

In the exemplary embodiment shown in the figure, both the analyte 2 and the dopant 4 are added together. However, the invention is not limited thereto. For example, in other embodiments, the dopant may be introduced from a source (not shown) located internal to the instrument. Thus, no limitations are intended.

Figure 2A:
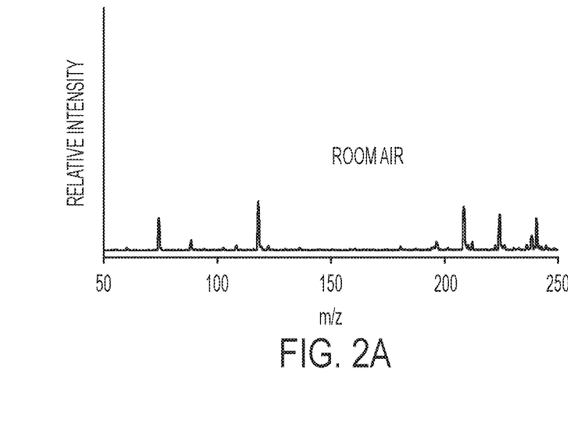
FIGS. 2A-2D show various MS spectra used to detect an exemplary OPC in concert with the present invention.
Figure 2B:
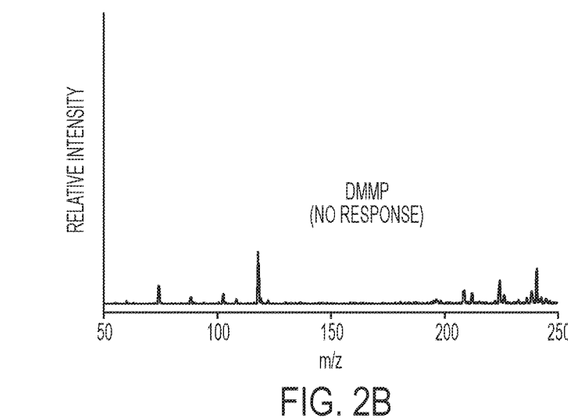
Figure 2C:
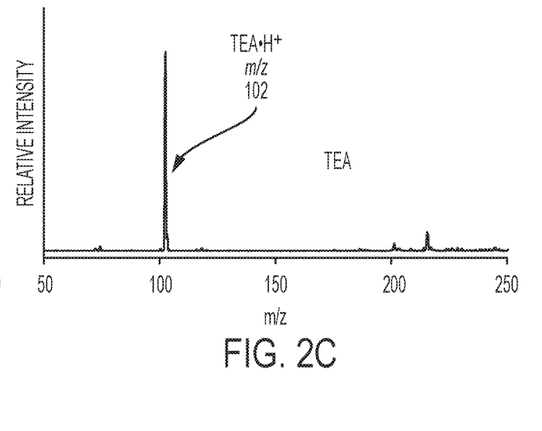
Figure 2D:
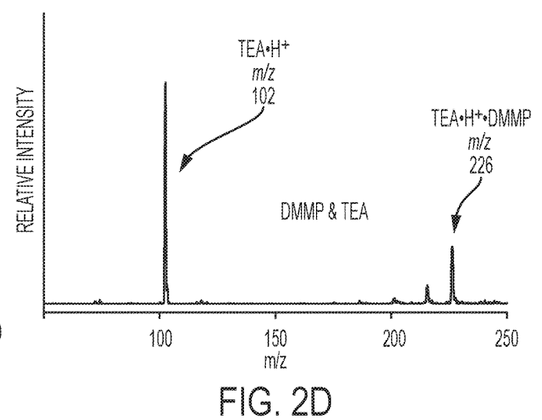

FIGS. 2A-2D are MS spectra (shown on the same x and y scales) showing peak intensities of selected vapors used to determine an exemplary OPC, dimethyl methyl phosphonate (DMMP), in concert with the present invention in the AFT-MS system of FIG. 1. FIG. 2A is an MS background spectrum of room air showing contaminates detected therein. FIG. 2B is an MS spectrum showing analysis of a trace level quantity of DMMP in room air. The spectrum is nearly identical to the background spectrum of FIG. 2A indicating that the analyte vapor DMMP is not detected alone at the trace level. However, the DMMP vapor can be detected in the presence of selected trialkylamine dopants. FIG. 2C shows an MS spectrum for a trace quantity of an exemplary trialkylamine dopant, triethylamine (TEA), in room air. Trialkylamines have high proton affinities relative to other species, and thus are observed at trace levels. A peak corresponding to the protonated TEA moiety [TEA·H$^+$] is positioned at an m/z value of 102. Although the TEA dopant has a high proton affinity and does not transfer the proton to DMMP, [TEA·H$^+$] does form an adduct [TEA·H$^+$·DMMP] with the OPC in the AFT leading into the MS that is used to selectively detect OPCs in the sample vapor. The adduct generates a characteristic peak that permits the OPC to be determined at trace quantities. FIG. 2D shows the MS peak corresponding to the adduct [TEA·H$^+$·DMMP] formed between the TEA dopant and the DMMP analyte of interest at an m/z value of 226. Presence of the adduct peak in the spectrum confirms the presence of the DMMP analyte in the vapor sample, which is not detected when the sample vapor is analyzed without the dopant therein.

Figure 3A:
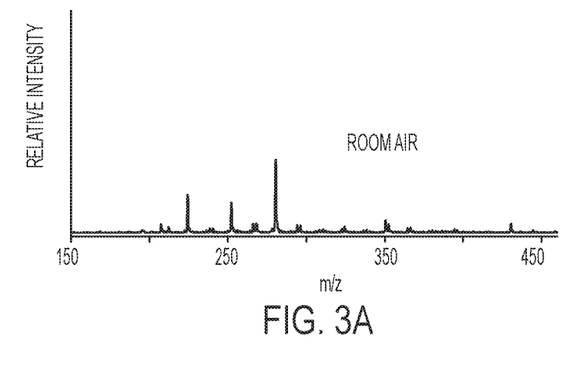
FIGS. 3A-3D are MS spectra used to detect another exemplary OPC in concert with the present invention.
Figure 3B:
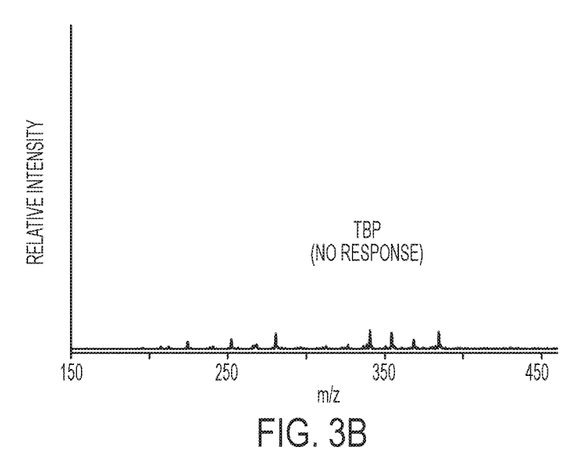
Figure 3C:
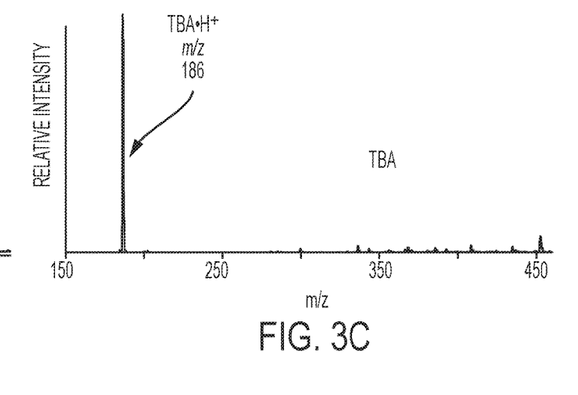
Figure 3D:
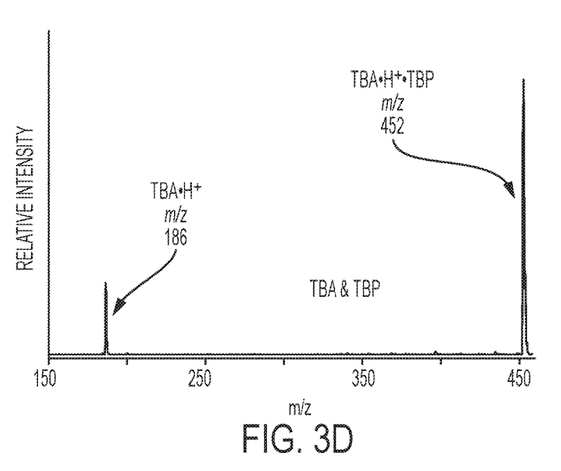

FIGS. 3A-3D are MS spectra showing peak intensities of selected vapors used to determine another exemplary OPC, tributyl phosphate (TBP), in the detection system of FIG. 1. FIG. 3A is an MS background spectrum of room air showing contaminates detected therein. FIG. 3B shows the MS spectrum resulting from analysis of a trace quantity of the analyte TBP in room air. As with DMMP described previously, the spectrum indicates that the analyte TBP is not detected at the trace level. However, TBP vapor can be detected in the presence of another trialkylamine dopant described hereafter. FIG. 3C shows the MS spectrum of a trace quantity of another trialkylamine dopant in room air, i.e., tributylamine (TBA), shown by the presence of a peak at an m/z value of 186 corresponding to the protonated TBA moiety [TBA·H$^+$]. The TBA dopant forms an adduct [TBA·H$^+$·TBP] with the OPC in the AFT leading into the MS that has a characteristic peak at an m/z value of 452 that permits the TBP analyte to be determined at trace quantities. FIG. 3D shows the MS peak corresponding to the [TBA·H$^+$·TBP] adduct formed between the TBA dopant ion and the TBP analyte of interest. The adduct peak in the spectrum confirms the presence of the TBP analyte in the sample, which was not previously detected in the sample vapor when analyzed alone.

Figure 4A:
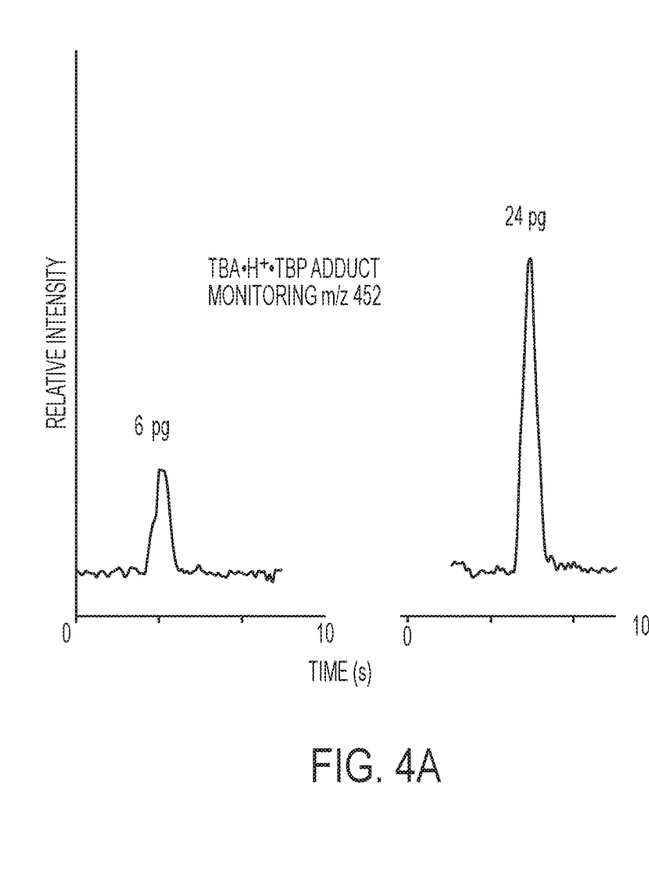
FIGS. 4A-4B show selected ion monitoring (SIM) peaks of adducts formed between Tributyl phosphate (TBP) and exemplary dopants at different TBP concentrations used to determine the TBP analyte.
Figure 4B:
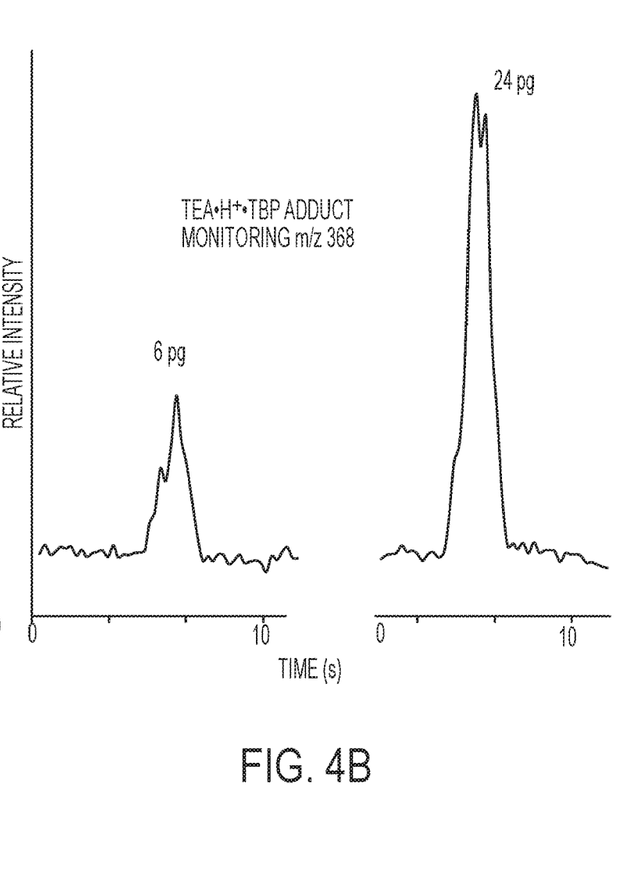

FIGS. 4A-4B show selected ion monitoring (SIM) peaks corresponding to adducts formed between TBP (the OPC) and the dopant TBA (FIG. 4A) and the dopant TEA (FIG. 4B), respectively, used to determine the TBP analyte at different concentrations [e.g., 6 picograms per microliter (6 pg/µL) and 24 pg/µL in methanol). 1 µL of each TBP solution was spiked onto a filament and released by desorption into the air stream at the inlet of the AFT leading to the MS system by heating the filament. Dopants were delivered from a permeation tube placed inside the AFT (FIG. 1). In FIG. 4A, a SIM peak monitored at an m/z value of 452 corresponding to the adduct [TBA·H$^+$·TBP] confirmed the presence of the TBP analyte in the vapor sample. In FIG. 4B, a SIM peak positioned at an m/z value of 368 corresponding to the adduct [TEA·H$^+$·TBP] was monitored, which confirmed the presence of the TBP analyte in the vapor sample.

Figure 5A:
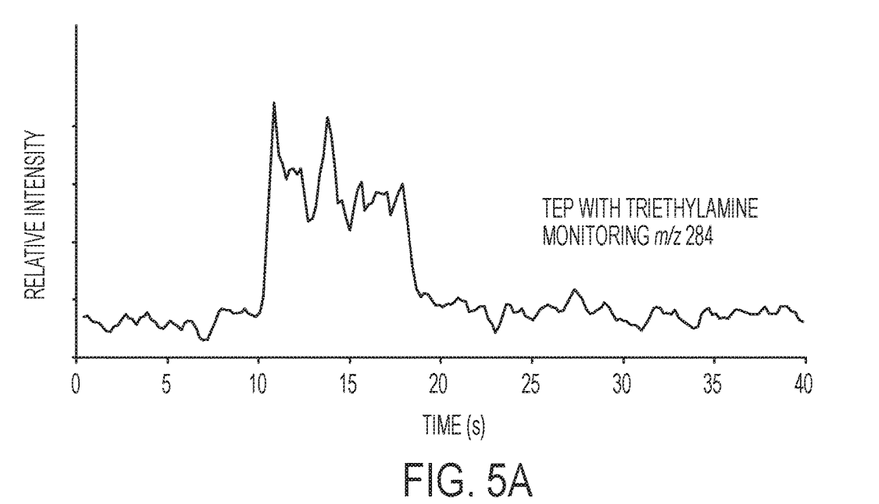
FIGS. 5A-5B show selected ion monitoring (SIM) peaks of adducts formed between Triethyl phosphate (TEP) with exemplary trimethylamine (TEA) and tributylamine (TBA) dopants used to determine the TEP analyte.
Figure 5B:
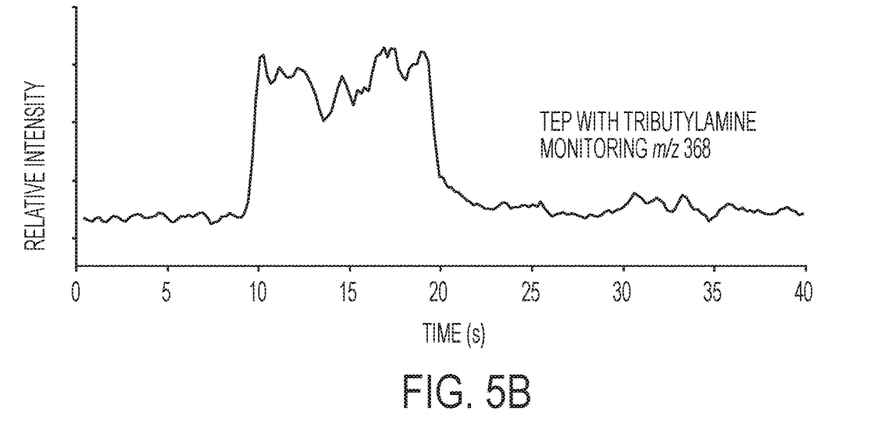

FIG. 5A shows a SIM peak at an m/z value of 284 corresponding to the adduct [TEA·H$^+$·TEP] formed between another exemplary OPC analyte, TEP, and another exemplary dopant, TEA, used to determine TEP at trace concentrations. The peak rises above the background when the permeation tube containing TEP is positioned in front of the AFT inlet and falls back to baseline when the TEP permeation tube is removed, for example, at 10 seconds and 20 seconds, respectively. Results yield a concentration for the TEP analyte of about 0.04 ng/L or about 5 parts-per-trillion (5 ppt). FIG. 5B shows a SIM peak at an m/z value of 368 that corresponds to the adduct [TBA·H$^+$·TEP] formed between the TEP analyte (OPC) and another exemplary dopant, TBA. The confirmatory peak again rises above the background when the permeation tube containing TEP is positioned in front of the AFT inlet and falls back to baseline when the TEP permeation tube is removed from the inlet. Results again yield a concentration for the TEP analyte of about 0.04 ng/L or about 5 parts-per-trillion (5 ppt).

Figure 6A:
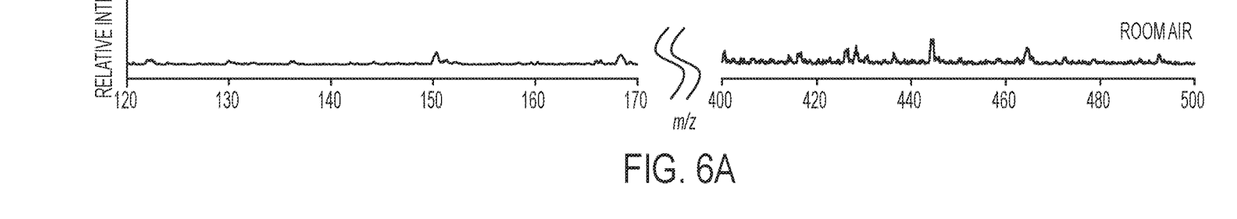
FIGS. 6A-6C are MS spectra used to detect the illicit drug methamphetamine in concert with the present invention.
Figure 6B:
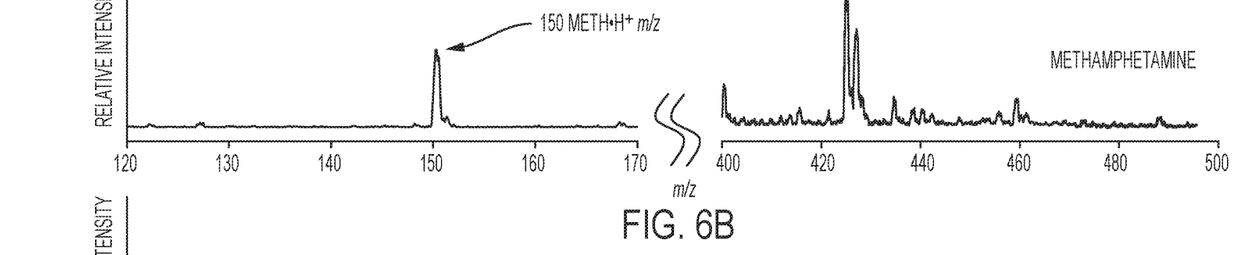
Figure 6C:
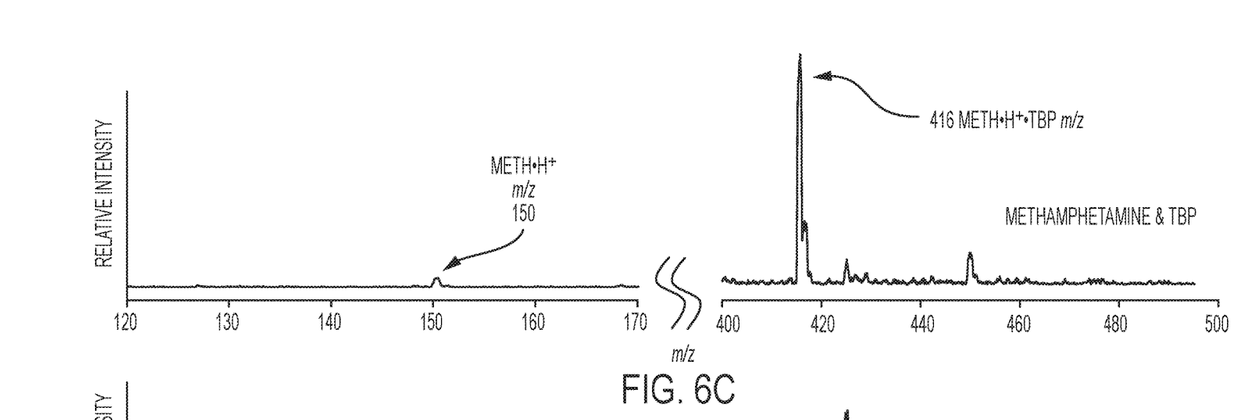

FIGS. 6A-6C are MS spectra showing vapor detection of an exemplary illicit drug, methamphetamine, in concert with the present invention. FIG. 6A is a background spectrum of room air showing trace level contaminates therein. FIG. 6B shows results from the analysis of a vapor sample containing a trace quantity of methamphetamine. A glass slide containing about 10 ug of the solid analyte of interest was presented at the AFT inlet. Methamphetamine vapor released from the glass slide was analyzed. In the figure, a peak corresponding to the [Meth·H$^+$] moiety positioned at an m/z of 150 is observed, which confirms the presence of the methamphetamine. FIG. 6C shows results from another test used to determine methamphetamine in a sample vapor. Here, a permeation tube containing the dopant TBP was positioned inside the AFT inlet, which delivered the dopant into the AFT. Methamphetamine vapor released from the solid on the glass slide combines with the TBP dopant released into the AFT forming an adduct [Meth·H$^+$·TBP] that generates a peak in the MS spectrum positioned at an m/z of 416. Presence of the peak confirms presence of the analyte of interest in the vapor sample. The confirmation peak includes a peak intensity that is enhanced by a factor of about 3 times, which permits a determination of the methamphetamine concentration therein. In this embodiment, the drug (an amine) is the analyte, and the trialkylphosphate (OPC) is the dopant. However, no limitations are intended.

Figure 7A:
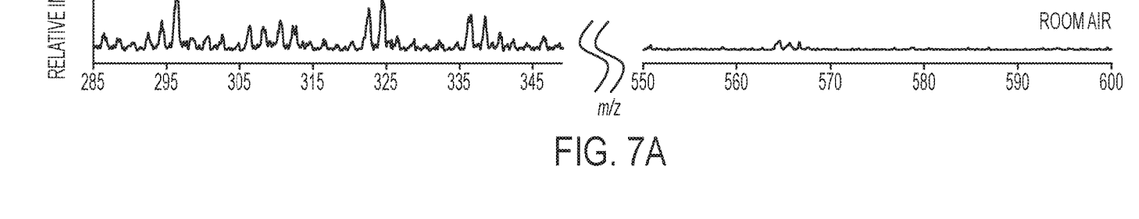
FIGS. 7A-7C are MS spectra used to detect the illicit drug cocaine in concert with the present invention.
Figures 7B, 7C:
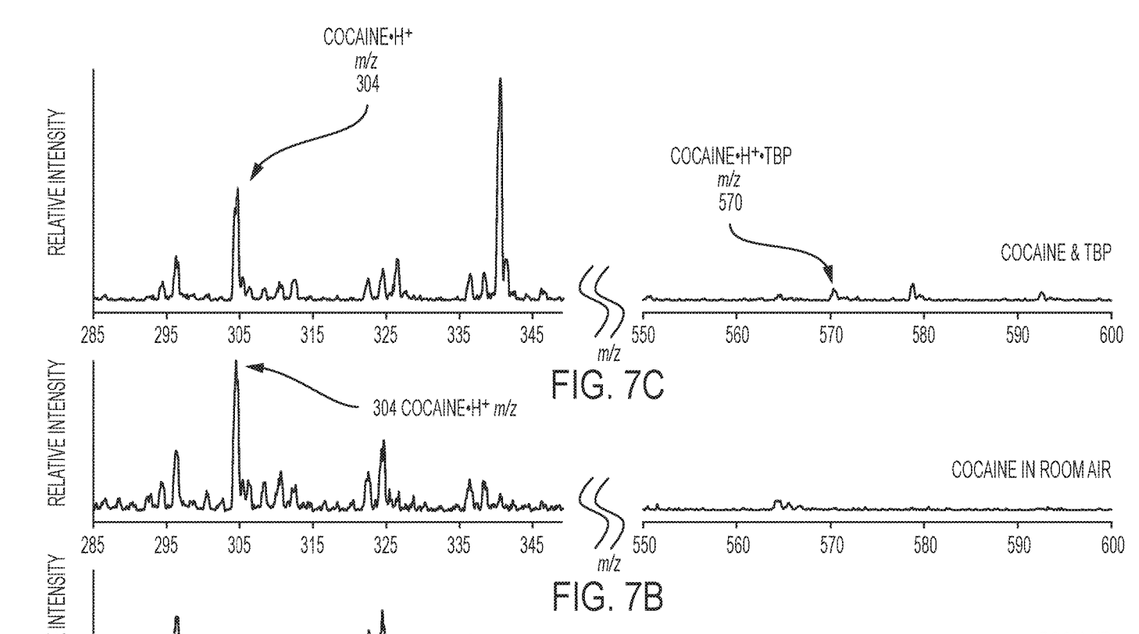

FIGS. 7A-7C are MS spectra showing results for detection of another illicit drug, cocaine, in concert with the present invention. FIG. 7A is a background spectrum of room air showing trace level contaminates therein. FIG. 7B shows analysis results of a trace quantity of cocaine vapor released from a glass slide containing about 10 ug of the solid sample into the AFT. As shown in the figure, a peak corresponding to the [Cocaine·H$^+$] moiety positioned at an m/z of 304 with a sufficiently strong intensity to identify the presence of cocaine in the vapor sample. However, as shown previously in FIG. 6C, use of the dopant TBP delivered, for example, from a permeation tube positioned inside the AFT yields a unique peak in the MS spectrum positioned at an m/z of 570, which corresponds to the adduct [Cocaine·H$^+$·TBP] formed in the AFT between the cocaine analyte and the TBP dopant that confirms presence of the cocaine analyte of interest in the vapor sample. The m/z 570 peak has a lower relative intensity, but does confirm presence of the illicit drug of interest by generating a unique adduct.

Figure 8A:
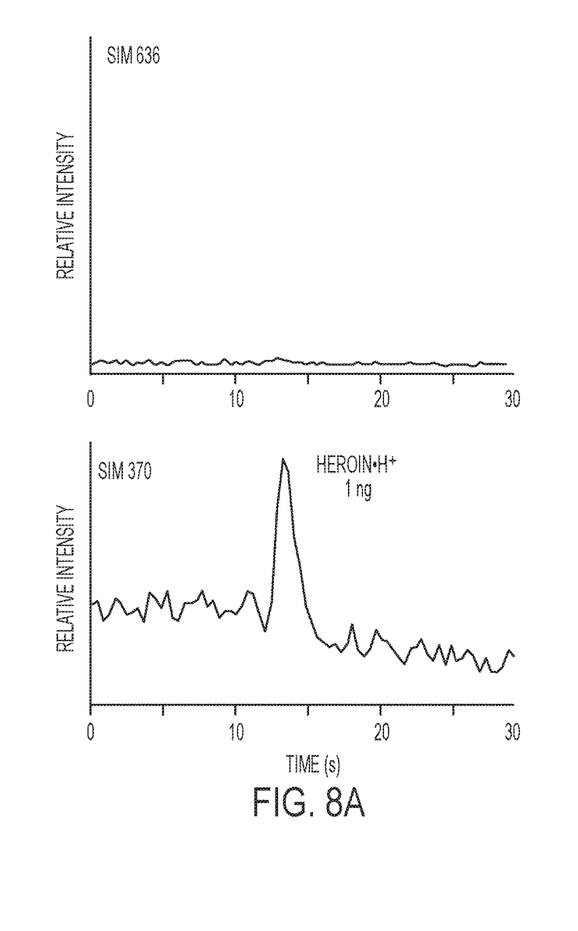
FIGS. 8A-8B show SIM peaks for detection of yet another illicit drug, heroin, in concert with the present invention.
Figure 8B:
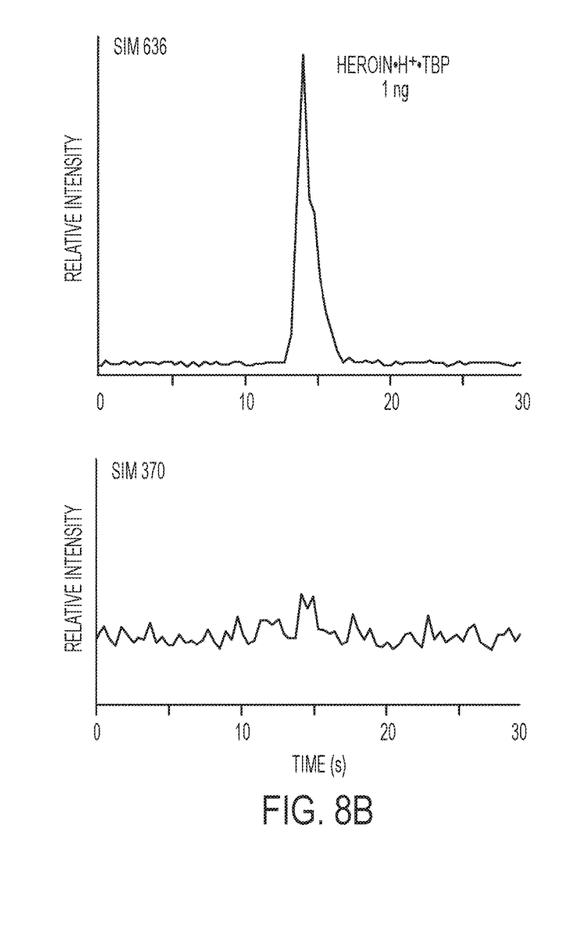

FIGS. 8A-8B show SIM peaks used for determination of a trace quantity [e.g., 1 ng] of heroin, another illicit drug, in concert with the present invention. In the test of FIG. 8A, 1 µL of a 1 ng/mL heroin sample in methanol was deposited onto a filament and the methanol was allowed to evaporate. The heroin residue (1 ng) was desorbed from the heated filament into the inlet of the AFT. No dopant was present in the AFT. Results of the SIM trace monitored at an m/z of 370 show presence of a protonated heroin moiety [Heroin·H$^+$], which appeared about 2 seconds after applying heat to the filament. As shown in FIG. 8A, the peak was observed at an arbitrary time of about 14 seconds. However, the peak corresponding to the [Heroin·H$^+$·TBP] adduct ion at an m/z of 636 is absent from the SIM trace, confirming the absence of the dopant in the vapor sample. In FIG. 8B, the test was repeated with a permeation tube containing TBP dopant positioned just inside the inlet of the AFT. Here, results show a relatively minor peak positioned at an m/z of 370 for the protonated heroin moiety and a new unique SIM peak observed at an m/z of 636 which corresponds to the adduct ion [Heroin·H$^+$·TBP] formed between the heroin analyte of interest and the TBP dopant in the AFT. Results show the adduct peak has an enhanced peak intensity of about 2 times, which permits determination of the heroin analyte of interest.

FIG. 9 compares IMS spectra collected with the IMS system of FIG. 1B for an exemplary OPC and the OPC in combination with an exemplary dopant used for detection of the OPC in concert with the present invention. In the absence of a dopant, reactant ions are protonated water molecules. The bottom spectrum demonstrates the result of introducing DMMP vapor into the system without a dopant present. A protonated monomer [DMMP·H$^+$] and a proton-bound dimer [(DMMP)$_2$·H$^+$] are observed. As shown in the top spectrum, addition of the dopant TEA results in the formation of a protonated [TEA·H$^+$] ion and a unique proton-bound adduct ion [DMMP·H$^+$·TEA]. The two DMMP peaks observed in the lower spectra combine after addition of the dopant into a single unique peak with an increased peak intensity that provides enhanced detection of the analyte.

The present invention has many applications in the detection of OPCs, illicit drugs, chemical weapons, and pesticides, such as in cargo, in baggage, and in screening mail. Non-contact detection would significantly improve interdiction efforts in these areas. For OPCs including pesticides and nerve agents, ability to detect these agents at or below part-per-trillion (ppt) levels will be highly valuable in any area where detection of these compounds below hazardous levels is desired.

EXAMPLE 1

Capped 2-mL vials containing about 0.5 mL dimethyl methylphosphonate (DMMP) as an exemplary OPC in one vial and about 0.5 mL triethylamine (TEA) as an exemplary trialkylamine dopant in a second vial were placed separately or together in front of the AFT inlet (FIG. 1). Trace vapors permeating through the septum of each vial were introduced into the air stream and subsequently into the reaction region of the AFT followed by detection in the MS instrument. A peak corresponding to the adduct [TEA·H$^+$·DMMP] formed between the DMMP analyte and the protonated TEA dopant ion confirmed presence of the OPC in the sample vapor at the trace quantity permitting detection of the analyte of interest. FIGS. 2A-2D present results.

EXAMPLE 2

A capped 2-mL vial containing about 0.5 mL undiluted TEA dopant was introduced in front of the AFT inlet (FIG. 1). 1 µL aliquots of tributylphosphate (TBP) solutions with different concentrations (e.g., 6 pg/µL or 24 pg/µL) were delivered in separate experiments to a coiled Ni-chrome wire filament connected to a 10V DC power supply that heated the wire desorbing the TBP at the inlet of the AFT introducing the vapor into the air stream along with the TEA dopant. The air stream flowed through the reaction region at a flow rate of about 10 L/min towards the inlet of the mass spectrometer. FIG. 4B presents results. Peaks corresponding to the adduct [TEA·H$^+$·TBP] formed between the TBP analyte and the protonated TEA dopant in the AFT confirmed presence of the TBP analyte (OPC) in the sample vapor. In this example, a spike consisting of 6 pg of the TBP analyte, a peak width of ~6 seconds, and an air volume of 1 L (i.e., at the 10 L/min flow rate) corresponds with an unoptimized detection limit for TBP of about 6 pg in 1 L, or approximately 780 parts-per-quadrillion (ppq). Calculation for the 24 pg spike was performed similarly and showed a larger response. Results show that with the addition of a dopant, unoptimized detection limits are below 6 pg or below 780 parts-per-quadrillion (ppq).

EXAMPLE 3

In a first experiment, TEP, an exemplary OPC, was delivered as an analyte vapor from a permeation tube positioned in front of the AFT inlet (FIG. 1) into an air stream flowing at a rate of about 6 L/min at room temperature. TEA, an exemplary dopant vapor, was delivered from a vial configured with a permeation septum positioned inside the AFT inlet upstream from the ionization source at room temperature. The permeation tube delivered the TEP at a rate of, for example, ~5 ng/min at a temperature of 50° C., for an estimated delivery at room temperature of ~0.6 ng/min. FIG. 5A shows a SIM peak at an m/z value of 284 corresponding to the adduct [TEA·H$^+$·TEP] formed between the TEP analyte and the TEA dopant. Results yield a concentration for the TEP analyte of about 0.04 ng/L or about 5 parts-per-trillion (5 ppt). In a second experiment, TEP (OPC) was delivered as an analyte vapor from a permeation tube positioned in front of the AFT inlet (FIG. 1) into an air stream flowing at a rate of about 6 L/min at room temperature (~0.6 ng/min). TBA, another exemplary dopant vapor, was delivered from a vial configured with a permeation septum positioned inside the AFT inlet upstream from the ionization source at room temperature. FIG. 5B shows a SIM peak at an m/z value of 368 that corresponds to the adduct [TBA·H$^+$·TEP] formed between the TEP analyte (OPC) and the TBA dopant. Results again yield a concentration for the TEP analyte of about 0.04 ng/L or about 5 parts-per-trillion (5 ppt)

EXAMPLE 4

A capped 4-mL vial containing about 0.5 mL undiluted tributylphosphate (TBP) dopant was introduced in front of the AFT inlet (FIG. 1). A 10 ug sample of cocaine residue was placed on an 18×18 mm glass slide and placed at the inlet of the AFT introducing the cocaine vapor into the air stream along with the TBP dopant. The air stream flowed through the reaction region at a flow rate of about 10 L/min towards the inlet of the mass spectrometer. FIG. 7C presents results. A peak corresponding to the adduct [Cocaine·H$^+$·TBP] at m/z 570 formed between the TBP dopant and the cocaine analyte in the AFT providing a confirmatory peak in addition to the protonated cocaine analyte at m/z 304 also visible in the same spectra. Equilibrium vapor pressure of cocaine (literature) ranges between 20 parts-per-trillion (ppt) and 400 ppt. Both of these peaks demonstrate the ability to detect cocaine vapor from a 10 ug residue introduced into a 10 L/min flow at ambient temperature of ~20° C. using a full scan of the mass spectrometer.

In another experiment, lower detection limits were achieved using selected ion monitoring (SIM). For example, 1 µL aliquots of cocaine solutions with different concentrations (e.g., 1, 10, and 50 pg/µL) were delivered in separate experiments to a coiled Ni-chrome wire filament connected to a 10V DC power supply that heated the wire desorbing the cocaine at the inlet of the AFT introducing the vapor into the air stream. The air stream flowed through the reaction region at a flow rate of about 10 L/min towards the inlet of the mass spectrometer. The 1 pg, 10 pg and 50 pg amounts of cocaine were detected above background with increasing peak heights corresponding to greater quantities of cocaine. Vapor concentrations of the sample containing 1 pg of cocaine in an air volume of about 0.5 L (calculated from the peak width of ~3 seconds) was introduced into the instrument at a 10 L/min flow rate, corresponding to an unoptimized detection limit for cocaine of ~160 parts-per-quadrillion (ppq).

EXAMPLE 5

A capped 4-mL vial containing about 0.5 mL tributylphosphate (TBP) dopant was introduced in front of the AFT inlet (FIG. 1). A 1 µL aliquot of a heroin solution with a concentration of 1 ng/µL was delivered to a coiled Ni-chrome wire filament. The filament was connected to a 10V DC power supply that heated the wire desorbing the heroin at the inlet of the AFT introducing the vapor into the air stream along with the TBP dopant. The air stream flowed through the reaction region at a flow rate of about 10 L/min towards the inlet of the mass spectrometer. FIG. 8B shows a peak at m/z 636 corresponding to the adduct [Heroin·H$^+$·TBP] formed between the TBP dopant and the heroin analyte in the AFT, which confirmed the presence of the heroin analyte in the sample vapor. The spike consisting of 1 ng of the heroin analyte, a peak width of ~5 seconds, and an air volume of about 0.8 L (i.e., at the 10 L/min flow rate) corresponds with an unoptimized detection for heroin of about 1 ng in 0.8 L, or approximately 81 parts-per-trillion (ppt). The observed peak is well above the detection limit of ~1 ppt based at the observed signal-to-noise ratio.

EXAMPLE 6

A hand-held ion mobility spectrometer (e.g., an LCD ABBII, Smiths Detection, Watford, U.K.) was used for detecting OPC vapors in the presence of various dopants. A flow diagram is presented in FIG. 1B. Modifications included removing ammonia vapors from the instrument by replacing the ammonia doped molecular sieve with fresh undoped molecular sieve several times over an extended period to change the reactant ion chemistry from ammonium ions to hydronium ions. The inlet of the IMS was placed loosely inside a 1-inch O.D. tube so that the IMS could sample vapors at a rate determined by its internal flow system. Clean, dry air was supplied in excess at a rate of 10 L/min flowing down the tube towards the IMS inlet with the excess venting around the inlet. The 1-inch tube contained two tees in series between the air supply and the inlet to the IMS. Each tee was capable of containing a 2 mL glass vial. A 2 mL vial containing DMMP with the cap removed was placed in the first tee and the resulting IMS spectra is shown in the bottom trace of FIG. 9, confirming detection of a protonated monomer and proton-bound dimer of DMMP. In a second experiment, an uncapped 2 mL vial containing ~0.5 mL TEA was placed in the second tee while the DMMP remained in the first tee thus providing a mixture of dopant and analyte vapors introduced to the IMS. The [TEA·H$^+$] ion is observed along with the [TEA·H$^+$·DMMP] adduct ion in the top trace of FIG. 9. For initial demonstration purposes, both the analyte and dopant were added together though it is envisioned that the dopant could be added internally.

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

What is claimed is:

1. A method, comprising:
   forming a proton-bound adduct ion between at least one organophosphorus compound (OPC) and at least one secondary or tertiary amine in a reaction region defined between an ionization source and an ion detector; and
   detecting the proton-bound adduct ion with the ion detector.

2. The method of claim 1, wherein the at least one secondary or tertiary amine includes a proton affinity greater than the at least one OPC.

3. The method of claim 1, wherein the at least one secondary or tertiary amine includes a proton affinity between 220 kcal/mol and 250 kcal/mol.

4. The method of claim 1, wherein the at least one OPC is an analyte and the at least one secondary or tertiary amine is a dopant and detecting the proton-bound adduct ion with the ion detector confirms the presence of the at least one OPC.

5. The method of claim 4, wherein the at least one OPC is a phosphonate or an organophosphate.

6. The method of claim 4, wherein the dopant is a dialkylamine, an alkyl-substituted derivative of pyridine, or a trialkylamine.

7. The method of claim 6, wherein the dialkylamine or the trialkylamine has R groups with between 1 and 12 carbons.

8. The method of claim 6, wherein the at least one OPC is detectable at 100 parts-per-quadrillion or better.

9. The method of claim 1, wherein the at least one secondary or tertiary amine is an illicit drug, and wherein the illicit drug is an analyte and the at least one OPC is a dopant and detecting the proton-bound adduct ion with the ion detector confirms the presence of the illicit drug.

10. The method of claim 9, wherein the at least one OPC is a phosphonate or an organophosphate.

11. The method of claim 9, wherein the illicit drug is heroin, cocaine, or methamphetamine.

12. The method of claim 9, wherein the illicit drug is detectable at 160 parts-per-quadrillion or better.

13. The method of claim 1, wherein the ion detector is a mass spectrometer or an ion mobility spectrometer.

14. The method of claim 1, further including ionizing a vapor sample comprising the at least one secondary or tertiary amine and/or the at least one OPC therein with the ionization source, wherein the at least one secondary or tertiary amine has a proton affinity greater than or equal to about 220 kcal/mol.

15. A method, comprising:
   ionizing a vapor sample with an ionization source, the vapor sample containing at least one organophosphorus compound (OPC) and at least one secondary or tertiary amine;
   introducing the ionized vapor sample containing the at least one OPC and at least one secondary or tertiary amine therein into a reaction region defined between the ionization source and an ion detector;
   forming at least one proton-bound adduct ion between the at least one OPC and the at least one secondary or tertiary amine therein; and
   detecting the at least one proton-bound adduct ion with the ion detector.

16. The method of claim 15, wherein the at least one secondary or tertiary amine has a proton affinity greater than the at least one OPC.

17. The method of claim 15, wherein the at least one secondary or tertiary amine has a proton affinity between 220 kcal/mol and 250 kcal/mol.

18. The method of claim 15, wherein the at least one OPC is an analyte and the at least one secondary or tertiary amine is a dopant and detecting the proton-bound adduct ion with the ion detector confirms the presence of the at least one OPC.

19. The method of claim 18, wherein the dopant is a dialkylamine, alkyl-substituted derivative of pyridine, or a trialkylamine.

20. The method of claim 18, wherein the dialkylamine or the trialkylamine has R groups with between 1 and 12 carbons.

21. The method of claim 15, wherein the at least one OPC is detectable at 100 parts-per-quadrillion or better.

22. The method of claim 15, wherein the at least one secondary or tertiary amine is an illicit drug, and wherein the illicit drug is an analyte and the at least one OPC is a dopant and detecting the proton-bound adduct ion with the ion detector confirms the presence of the illicit drug.

23. The method of claim 22, wherein the illicit drug is detectable at or greater than 160 parts-per-quadrillion.

24. The method of claim 15, wherein the ion detector is a mass spectrometer or an ion mobility spectrometer.

25. The method of claim 7, wherein the dialkylamine is diethylamine, diisopropyl amine, diethylmethyl amine, or combinations thereof, or wherein the trialkylamine is triethylamine, tripropylamine, tributylamine, trioctylamine, tridecylamine, tridodecylamine, or combinations thereof.

26. The method of claim 20, wherein the dialkylamine is diethylamine, diisopropyl amine, diethylmethyl amine, or combinations thereof, or wherein the trialkylamine is triethylamine, tripropylamine, tributylamine, trioctylamine, tridecylamine, tridodecylamine, or combinations thereof.

* * * * *